(12) United States Patent
Culbert et al.

(10) Patent No.: US 7,070,601 B2
(45) Date of Patent: Jul. 4, 2006

(54) LOCKING PLATE FOR BONE ANCHORS

(75) Inventors: Brad S. Culbert, Rancho Santa Margarita, CA (US); Bruce E. Stevens, Laguna Niguel, CA (US)

(73) Assignee: Triage Medical, Inc., Irvine, CA (US)

( * ) Notice: Subject to any disclaimer, the term of this patent is extended or adjusted under 35 U.S.C. 154(b) by 0 days.

(21) Appl. No.: 10/756,892

(22) Filed: Jan. 14, 2004

(65) Prior Publication Data

US 2004/0181222 A1 Sep. 16, 2004

Related U.S. Application Data

(60) Provisional application No. 60/440,765, filed on Jan. 16, 2003.

(51) Int. Cl.
*A61B 17/76* (2006.01)

(52) U.S. Cl. .............................. 606/71; 606/65; 606/73

(58) Field of Classification Search ................... 606/65, 606/66, 67, 68, 69, 70, 71, 72, 73
See application file for complete search history.

(56) References Cited

U.S. PATENT DOCUMENTS

| | | | |
|---|---|---|---|
| 1,802,560 A | 4/1931 | Kerwin |
| 2,077,804 A | 4/1937 | Morrison |
| 2,121,193 A | 6/1938 | Hanicke |
| 2,485,531 A | 10/1949 | Dzus et al. |
| 2,489,870 A | 10/1949 | Dzus |
| 3,115,804 A | 12/1963 | Johnson |
| 3,489,143 A | 1/1970 | Holloran |
| 4,052,988 A | 10/1977 | Doddi et al. |
| 4,175,555 A | 11/1979 | Herbert |
| 4,262,665 A | 4/1981 | Roalstad et al. |
| 4,275,717 A | 6/1981 | Bolesky |
| 4,463,753 A | 8/1984 | Gustilo |
| 4,537,185 A | 8/1985 | Stednitz |
| 4,632,101 A | 12/1986 | Freedland |
| 4,640,271 A | 2/1987 | Lower |
| 4,667,663 A | 5/1987 | Miyata |
| 4,688,561 A | 8/1987 | Reese |
| 4,721,103 A | 1/1988 | Freedland |
| 4,743,257 A | 5/1988 | Tormala et al. |
| 4,790,304 A | 12/1988 | Rosenberg |
| 4,796,612 A | 1/1989 | Reese |
| 4,815,909 A | 3/1989 | Simons |
| 4,827,917 A | 5/1989 | Brumfield |

(Continued)

FOREIGN PATENT DOCUMENTS

CN 1177918 A 4/1998

(Continued)

*Primary Examiner*—David O. Reip
(74) *Attorney, Agent, or Firm*—Knobbe, Martens, Olson & Bear, LLP.

(57) ABSTRACT

Disclosed is a bone fracture fixation system, such as for reducing and compressing fractures in the proximal femur. The fixation system includes a plurality of elongated bodies with a helical cancellous bone anchor on a distal end of each of the bodies. An axially moveable plate with a plurality of openings is carried by the proximal end of the elongated bodies. The elongated bodies are rotated into position across the fracture or separation between adjacent bones and into the adjacent bone or bone fragment, and the plate is distally advanced to apply secondary compression and lock the device into place. The device may also be used for soft tissue attachments.

34 Claims, 9 Drawing Sheets

U.S. PATENT DOCUMENTS

| | | | |
|---|---|---|---|
| 4,858,601 | A | 8/1989 | Glisson |
| 4,873,976 | A | 10/1989 | Schreiber |
| 4,898,186 | A | 2/1990 | Ikada et al. |
| 4,903,692 | A | 2/1990 | Reese |
| 4,917,554 | A | 4/1990 | Bronn |
| 4,940,467 | A | 7/1990 | Tronzo |
| 4,959,064 | A | 9/1990 | Engelhardt |
| 4,968,317 | A | 11/1990 | Tormala et al. |
| 4,978,349 | A | 12/1990 | Frigg |
| 4,988,351 | A | 1/1991 | Paulos et al. |
| 5,013,315 | A | 5/1991 | Barrows |
| 5,013,316 | A | 5/1991 | Goble et al. |
| 5,059,193 | A | 10/1991 | Kuslich |
| 5,062,849 | A | 11/1991 | Schelhas |
| 5,092,891 | A | 3/1992 | Kummer et al. |
| 5,098,433 | A | 3/1992 | Freedland |
| 5,098,435 | A | 3/1992 | Stednitz et al. |
| 5,122,133 | A | 6/1992 | Evans |
| 5,122,141 | A | 6/1992 | Simpson et al. |
| 5,167,663 | A | 12/1992 | Brumfield |
| 5,167,664 | A | 12/1992 | Hodorek |
| 5,217,462 | A | 6/1993 | Asnis et al. |
| 5,242,447 | A | 9/1993 | Borzone |
| 5,246,441 | A | 9/1993 | Ross et al. |
| 5,250,049 | A | 10/1993 | Michael |
| 5,300,074 | A | 4/1994 | Frigg |
| 5,312,410 | A | 5/1994 | Miller et al. |
| 5,334,204 | A | 8/1994 | Clewett et al. |
| 5,364,398 | A | 11/1994 | Chapman et al. |
| 5,370,646 | A | 12/1994 | Reese et al. |
| 5,370,661 | A | 12/1994 | Branch |
| 5,382,248 | A | 1/1995 | Jacobson et al. |
| 5,449,359 | A | 9/1995 | Groiso |
| 5,449,361 | A | 9/1995 | Preissman |
| 5,452,748 | A | 9/1995 | Simmons et al. |
| 5,470,333 | A | 11/1995 | Ray |
| 5,498,265 | A | 3/1996 | Asnis et al. |
| 5,501,695 | A | 3/1996 | Anspach, Jr. et al. |
| 5,520,690 | A | 5/1996 | Errico et al. |
| 5,536,127 | A | 7/1996 | Pennig |
| 5,545,164 | A | 8/1996 | Howland |
| 5,549,610 | A | 8/1996 | Russell et al. |
| D374,287 | S | 10/1996 | Goble et al. |
| 5,591,168 | A * | 1/1997 | Judet et al. .................... 606/65 |
| 5,618,142 | A | 4/1997 | Sonden et al. |
| 5,618,314 | A | 4/1997 | Harwin et al. |
| 5,626,613 | A | 5/1997 | Schmieding |
| 5,628,751 | A | 5/1997 | Sander et al. |
| 5,643,320 | A | 7/1997 | Lower et al. |
| 5,662,683 | A | 9/1997 | Kay |
| 5,669,915 | A | 9/1997 | Caspar et al. |
| 5,713,903 | A | 2/1998 | Sander et al. |
| 5,720,753 | A | 2/1998 | Sander et al. |
| 5,725,541 | A | 3/1998 | Anspach, III et al. |
| 5,728,097 | A | 3/1998 | Mathews |
| 5,728,116 | A | 3/1998 | Rosenman |
| 5,735,853 | A | 4/1998 | Olerud |
| 5,741,282 | A | 4/1998 | Anspach, III et al. |
| 5,772,662 | A | 6/1998 | Chapman et al. |
| 5,782,865 | A | 7/1998 | Grptz |
| 5,849,004 | A | 12/1998 | Bramlet |
| 5,871,485 | A | 2/1999 | Rao et al. |
| 5,893,850 | A | 4/1999 | Cachia |
| 5,904,696 | A | 5/1999 | Rosenman |
| 5,908,422 | A | 6/1999 | Bresina |
| 5,928,235 | A | 7/1999 | Friedl |
| 5,928,244 | A | 7/1999 | Tovey et al. |
| 5,935,129 | A | 8/1999 | McDevitt et al. |
| 5,947,999 | A | 9/1999 | Groiso |
| 5,948,000 | A | 9/1999 | Larsen et al. |
| 5,954,722 | A | 9/1999 | Bono |
| 5,954,747 | A | 9/1999 | Clark |
| 5,957,924 | A | 9/1999 | Tormala et al. |
| 5,968,044 | A | 10/1999 | Nicholson et al. |
| 5,976,139 | A | 11/1999 | Bramlet |
| 5,984,927 | A | 11/1999 | Wenstrom, Jr. et al. |
| 5,984,966 | A | 11/1999 | Kiena et al. |
| 5,989,255 | A | 11/1999 | Pepper et al. |
| 5,993,459 | A | 11/1999 | Larsen et al. |
| 5,997,538 | A | 12/1999 | Asnis et al. |
| 5,997,541 | A | 12/1999 | Schenk |
| 6,001,100 | A | 12/1999 | Sherman et al. |
| 6,001,101 | A | 12/1999 | Augagneur et al. |
| 6,004,327 | A | 12/1999 | Asnis et al. |
| 6,005,161 | A | 12/1999 | Brekke et al. |
| 6,007,566 | A | 12/1999 | Wenstorm, Jr. |
| 6,007,580 | A | 12/1999 | Lehto et al. |
| 6,010,513 | A | 1/2000 | Tormala et al. |
| 6,015,410 | A | 1/2000 | Tormala et al. |
| 6,019,762 | A | 2/2000 | Cole |
| 6,030,162 | A | 2/2000 | Huebner |
| 6,036,701 | A | 3/2000 | Rosenman |
| 6,068,648 | A | 5/2000 | Cole et al. |
| 6,083,244 | A | 7/2000 | Lubbers et al. |
| 6,123,711 | A | 9/2000 | Winters |
| 6,126,661 | A | 10/2000 | Faccioli et al. |
| 6,162,234 | A | 12/2000 | Freedland et al. |
| 6,168,595 | B1 | 1/2001 | Durham et al. |
| 6,183,472 | B1 | 2/2001 | Lutz |
| 6,183,474 | B1 | 2/2001 | Bramlet et al. |
| 6,248,108 | B1 | 6/2001 | Tormala et al. |
| 6,306,136 | B1 | 10/2001 | Baccelli |
| 6,319,254 | B1 | 11/2001 | Giet et al. |
| 6,355,043 | B1 | 3/2002 | Adam |
| 6,361,537 | B1 | 3/2002 | Anderson |
| 6,371,989 | B1 | 4/2002 | Chauvin et al. |
| 6,423,061 | B1 | 7/2002 | Bryant |
| 6,423,067 | B1 | 7/2002 | Eisermann |
| 6,458,134 | B1 | 10/2002 | Songer et al. |
| 6,468,277 | B1 | 10/2002 | Justin et al. |
| 6,468,309 | B1 | 10/2002 | Lieberman |
| 6,491,714 | B1 | 12/2002 | Bennett |
| 6,506,192 | B1 | 1/2003 | Gertzman et al. |
| 6,511,481 | B1 | 1/2003 | Von Hoffmann et al. |
| 6,517,543 | B1 | 2/2003 | Berrevoets et al. |
| 6,527,774 | B1 | 3/2003 | Lieberman |
| 6,544,265 | B1 | 4/2003 | Lieberman |
| 6,547,793 | B1 | 4/2003 | McGuire |
| 6,551,319 | B1 | 4/2003 | Lieberman |
| 6,551,322 | B1 | 4/2003 | Lieberman |
| 6,558,389 | B1 | 5/2003 | Clark et al. |
| 6,579,293 | B1 | 6/2003 | Chandran |
| 6,582,453 | B1 | 6/2003 | Tran et al. |
| 6,585,730 | B1 | 7/2003 | Foerster |
| 6,585,740 | B1 | 7/2003 | Schlapfer |
| 6,589,249 | B1 | 7/2003 | Sater et al. |
| 6,599,297 | B1 | 7/2003 | Carlsson et al. |
| 6,635,059 | B1 | 10/2003 | Randall et al. |
| 6,692,499 | B1 | 2/2004 | Tormalaet et al |
| 6,875,215 | B1 | 4/2005 | Taras et al. |
| 6,916,323 | B1 | 7/2005 | Kitchens |
| 6,921,403 | B1 | 7/2005 | Cragg et al. |
| 6,945,975 | B1 | 9/2005 | Dalton |
| 6,949,100 | B1 | 9/2005 | Venturini |
| 2002/0055740 | A1 | 5/2002 | Lieberman |
| 2002/0143335 | A1 | 10/2002 | Von Hoffman et al. |

FOREIGN PATENT DOCUMENTS

| | | | |
|---|---|---|---|
| EP | 0525352 A1 | 2/1993 | |
| EP | 1046376 A1 | 4/2000 | |
| EP | 0853929 B1 | 9/2002 | |
| EP | 1378205 A1 | 7/2003 | |
| FR | 2699065 | 12/1992 | |

| | | | | | |
|---|---|---|---|---|---|
| FR | 2728778 | 12/1994 | GB | 2173565 A | 10/1986 |
| FR | 2745709 | 3/1996 | GB | 2173655 | 10/1986 |
| FR | 2800601 | 11/1999 | JP | 64-52439 | 2/1989 |
| FR | 2801189 | 11/1999 | WO | WO 91/09572 | 12/1989 |
| FR | 2808182 | 4/2000 | | | |
| GB | 2157788 A | 10/1985 | | | |

* cited by examiner

LOCKING PLATE FOR BONE ANCHORS

PRIORITY INFORMATION

This application claims the priority benefit under 35 U.S.C. § 119(e) of Provisional Application 60/440,765, filed Jan. 16, 2003.

BACKGROUND OF THE INVENTION

1. Field of the Invention

The present invention relates to internal bone fracture fixation devices. In one application, the present invention relates to bone fracture fixation devices and methods adapted for fixation, among other fractures, of femoral neck and other proximal femoral fractures.

2. Description of the Related Art

The femur, otherwise known as the thigh bone, generally comprises an elongate shaft extending from the hip to the knee. The proximal end of the shaft includes a head, a neck, a greater trochanter and a lesser trochanter. The head of the femur fits into the acetabular cup of the hip bone to form a ball and socket joint at the hip. The distal end of the femur includes a medial condyle and a lateral condyle. The condyles engage an upper end of the tibia to form the knee joint. Overall, the femur is the longest and strongest bone in the skeleton. However, portions of the femur are extremely susceptible to fracturing.

Pertrochanteric fractures among geriatric patients are the most frequent in connection with those of the region of the neck of the bone. The advanced age and the pathologies which are encountered in these patients make a timely stabilization of skeletal injuries necessary in order to reduce to a minimum the bed confinement and the rehabilitation times. Preferably, devices and procedures are utilized which minimize complications brought about by the so-called immobilization syndrome, which may be lethal for patients in delicate metabolical circumstances. It is also preferable to reduce to a minimum blood losses related to surgical intervention. At the same time, the syntheses means utilized must be stable in order to allow the patient to very timely assume a seated position and, two or three days following the intervention, to reassume an erect posture with progressive bearing of weight.

Internal fixation of femoral fractures in general is one of the most common orthopedic surgical procedures. Fractures of the femur occur in both the proximal portion of the femur and the distal portion of the femur. Fractures of the proximal portion of the femur (hip fractures) are generally classified as femoral neck fractures (capital or sub-capital), intertrochanteric fractures and subtrochanteric fractures. Fractures of the distal portion of the femur (knee fractures) are referred to as supracondylar fractures. Supracondylar fractures generally extend vertically between the condyles at the lower end of the femur to separate the distal portion of the femur into two main bone fragments. A fracture line may be further comminuted to create a plurality of smaller bone fragments. Fractures of the femur which extend into the neck of the bone are generally more difficult to treat than fractures restricted to the shaft of the femur.

Operative treatment of the fractures requires that the fractures be internally fixed and possibly compressed. Fractures of the neck, head or trochanters of the femur have been treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint weight bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Thus, notwithstanding the variety of efforts in the prior art, there remains a need for an orthopedic fixation device with improved locking force such as within the femoral head in a femoral neck application, which resists migration and rotation, and which can be easily and rapidly deployed within the bone.

SUMMARY OF THE INVENTION

It is often desirable to insert a plurality of implants into the bone to stabilize a fracture. For example, triangulation of implants (i.e., arranging the implants in a triangular pattern) is a particularly effective way of treating proximal fractures of the femur (i.e., capital, sub-capital, and intertrochanteric fractures). Applicant has recognized that it would be advantageous to have a common device, which preferably could be used to couple the implants together while also securing the implant within the bone. Such a device would preferably simplify the procedure of installing the plurality of implants by providing a predetermined spatial and/or angular relationship between the implants, while increasing overall stability and resistance to failure.

In accordance with one aspect of the present invention, a femoral neck fracture fixation system comprises a plurality of elongated bodies. Each elongated body has a proximal end and a distal end. A distal anchor is provided on the distal end of each of the elongated bodies. A first retention structure is provide on each of the elongated bodies, proximal to the distal anchor. The system also includes a plate with a plurality of openings. The openings are configured such that the plate can be moveably carried by the plurality elongated bodies. The plate is movable in the distal direction with respect to the elongated bodies and the retention structure resists proximal movement of the plate with respect the elongated bodies.

In accordance with another aspect of the invention a bone fracture fixation system comprises a plurality of elongated bodies, each having a proximal end and a distal end. A cancellous bone anchor is provided on the distal end the elongated bodies. The device also includes a plate having at least two openings and that is axially movably carried on the elongated bodies. Complimentary surface structures are provided in between the elongated bodies and the plate. The complimentary surface structures permit advancing the plate in the distal direction to tighten the fixation device but resist axial proximal movement of the plate with respect to the elongated bodies.

In accordance with yet another aspect of the invention, a method for treating a femoral fracture comprises drilling a plurality of bores distally into the femur in the direction of a fracture, advancing a fixation device into each of the bores, rotating each of the fixation devices to engage bone distal to the fracture, and advancing a plate with a plurality of openings distally along the fixation devices to compress the fracture.

In accordance with still yet another aspect of the invention, a method of securing a first bone fragment to a second bone fragment comprises drilling a plurality of bores through the first bone fragment in the direction of the second bone fragment, advancing a fixation device through each of the bores, rotating at least a first portion of each of the fixation devices to secure the fixation devices to the second fragment, and axially advancing a plate with a plurality of openings over at least a second portion of each of the fixation devices to engage the first fragment.

Further features and advantages of the present invention will become apparent to those of skill in the art in view of the detailed description of preferred embodiments which follows, when considered together with the attached drawings and claims.

DETAILED DESCRIPTION OF THE PREFERRED EMBODIMENT

Figure 1:
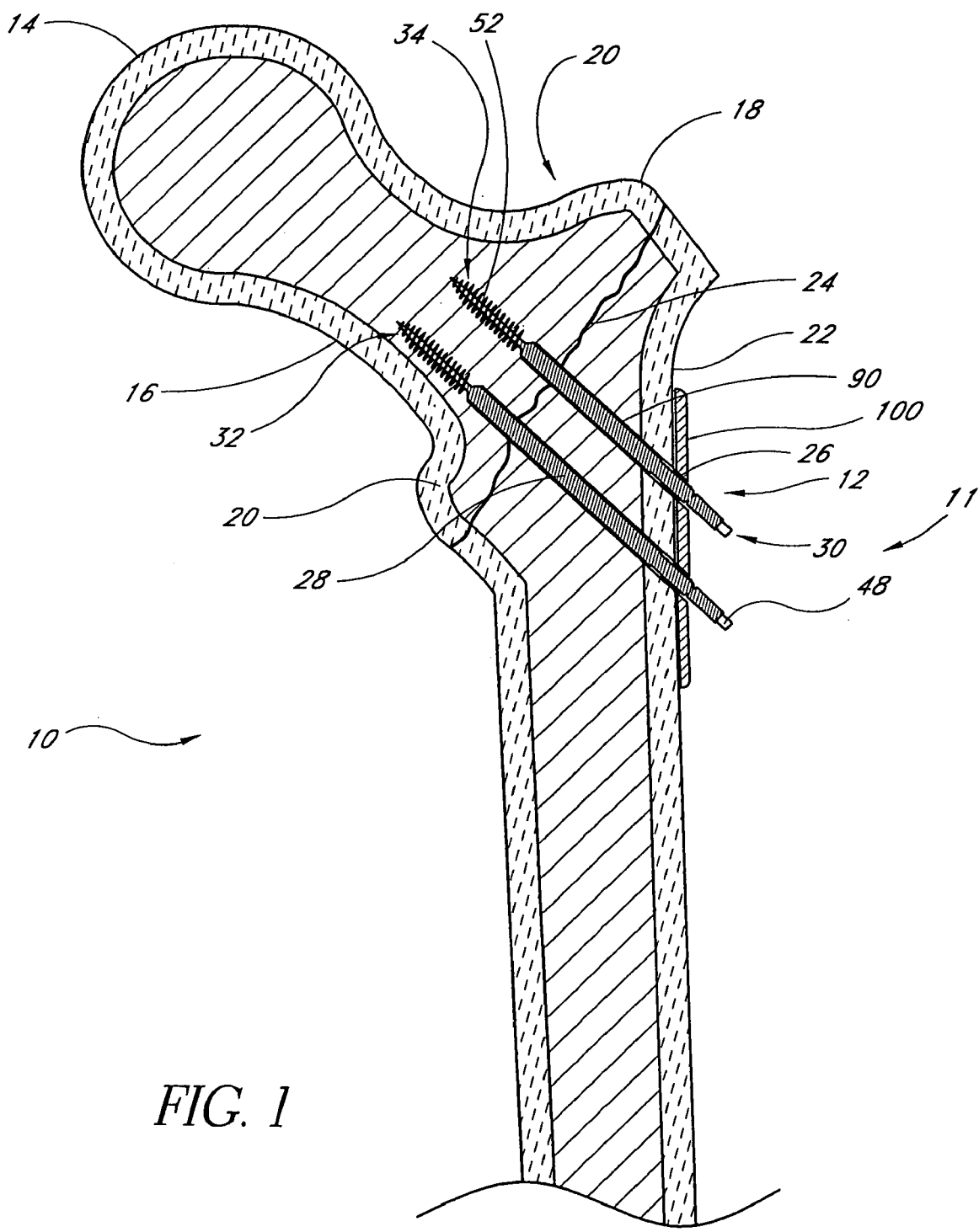
FIG. 1 is a posterior elevational posterior cross section through the proximal portion of the femur, having at least two femoral neck fracture fixation pins positioned therein and coupled together by a locking plate.

Although the fixation devices of the present invention will be disclosed primarily in the context of fractures of the proximal femur, the methods and structures disclosed herein are intended for application in any of a wide variety of bones and fractures, as will be apparent to those of skill in the art in view of the disclosure herein. In general, the present invention is most beneficial in an application in which it is desired to repeatably maintain a predetermined spatial and/or angular relationship between two or more bone anchors or pins.

Potential applications include, for example, a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent, absorbable, or combinations.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. Fractures and osteotomies of the mid and hind foot, tarsal arthrodesis and osteotomy, or others as are known to those with skill in the art. One example is the fixation of the medial malleolar avulsion fragment fixation.

The fixation device of the present invention may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, or the pin and or collar may be modified to accept a suture or other material for facilitation of this attachment.

Specific examples include attachment of the posterior tibial tendon to the navicular bone in the Kidner operation. This application may be accomplished using an appropriately sized implant of the present invention along with a washer with distally extending soft tissue spikes. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The fixation devices can also be used to aid bone fusion between adjacent bones, bone fragments or any of a variety of articulating joints, such as, for example, a first and a second adjacent vertebral bodies of the spine.

The fixation devices may be used in combination with semi tubular, one-third tubular and dynamic compression plates, both of metallic and absorbable composition, if the collar is modified to match the opening on the plate.

The cannulated design disclosed below can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods may be included for wound prophylaxis during transport.

FIG. 1 illustrates a posterior side elevational view of the proximal portion of a femur 10 and a fixation system 11 having certain features and advantages according to the present invention. The proximal end of the femur 10 comprises a head 14 connected by way of a neck 16 to the long body or shaft 17 of the femur 10. As illustrated in FIG. 1, the neck 16 is smaller in diameter than the head 14. The neck 16 and head 14 also lie on an axis which, on average in humans, crosses the longitudinal axis of the body 17 of the femur 10 at an angle of about 126°. The risk of fracture at the neck 16 is thus elevated, among other things, by the angular departure of the neck 16 from the longitudinal axis of the body 17 of femur 10 and also the reduced diameter of the neck 16 with respect to the head 14.

The greater trochanter 18 extends outwardly above the junction of the neck 16 and the body 17 of the femur 10. On the medial side of the greater trochanter 18 is the trochanteric fossa 20. This depression accommodates the insertion of the obturator externus muscle. The lesser trochanter 21 is located posteromedially at the junction of the neck 16 and the body 17 of the femur 10. Both the greater trochanter 18 and the lesser trochanter 21 serve for the attachment of muscles. On the posterior surface of the femur 10 at about the same axial level as the lesser trochanter 21 is the gluteal tuberosity 22, for the insertion of the gluteus maximus muscle. Additional details of the femur are well understood in the art and not discussed in further detail herein.

FIG. 1 illustrates a subcapital femoral neck fracture 24. Fractures of the proximal portion of the femur 10 are generally classified as capital or subcapital femoral neck fractures, intertrochanteric fractures and subtrochanteric fractures. All of these fractures will be deemed femoral neck fractures for the purpose of describing the present invention.

As mentioned above, for some applications it is desirable to insert a plurality of fixation devices into the femur 10. It also may be desirable to ensure that the plurality of fixation devices are positioned at predetermined locations and/or angles with respect to each other. For example, the use of three bone fixation devices arranged in a triangular pattern is an effective way of treating proximal fractures of the femur (e.g., capital, sub-capital and intertrochanteric fractures). Such arrangements are particularly useful if the clinician determines, that based upon the nature of the fracture 24, there is a possibility that the head 14 of the femur 10 could rotate about a single fixation pin 12. Even minor rotation can inhibit the healing of the fracture and significant rotation can result in failure of the fixation device or necrosis of the femoral head.

As such, in the illustrated embodiment, the fixation system 11 includes three fixation pins 12 (the third pin 12 is not illustrated in FIG. 1) and a locking plate 26 having certain features and advantages according to the present invention. As shown in FIGS. 1–2B, the fixation pins 12 comprise a body 28 extending between a proximal end 30 and a distal end 32. The length, diameter and construction materials of the body 28 can be varied, depending upon the intended clinical application. In embodiments optimized for various fractures in an adult human population, the body 28 will generally be within the range of from about 6 mm to about 150 mm in length after sizing, and within the range of from about 2 mm to about 12 mm in maximum diameter. The major diameter of the helical anchor, discussed below, may be within the range of from about 2.0 mm to about 15 mm. In general, the appropriate dimensions of the body 28 will vary, depending upon the specific fracture. In rough terms, for a malleolar fracture, shaft diameters in the range of from about 3 mm to about 4.5 mm may be used, and lengths within the range of from about 20 mm to about 70 mm. For condylar fractures, shaft diameters within the range of from about 3.5 mm to about 8.0 mm may be used with lengths within the range of from about 25 mm to about 70 mm. For colles fractures (distal radius and ulna), diameters within the range of from about 2.0 mm to about 4.5 mm may be used with any of a variety of lengths within the range of from about 6 mm to about 70 mm.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Additional details of the distal bone anchor are described below. In general, in a femoral neck application, distal bone anchor 34 is adapted to be rotationally inserted into the cancellous bone within the head 14 of the femur 10, to retain the fixation device 12 within the femoral head.

The proximal end 30 of the fixation pin 12 extends through the locking plate 26. The locking plate 26 is axially moveable in a distal direction along the body 28, to permit compression of the fracture 24 as will be apparent from FIG. 1 and the description below. As will be explained below, complementary locking structures such as threads or ratchet like structures between the locking plate 26 and the body 28 resist proximal movement of the body 28 with respect to the locking plate 36 under normal use conditions. The body 28 can be axially moved with respect to the locking plate 26 with or without rotation as will be explained in more detail below.

Figure 3:
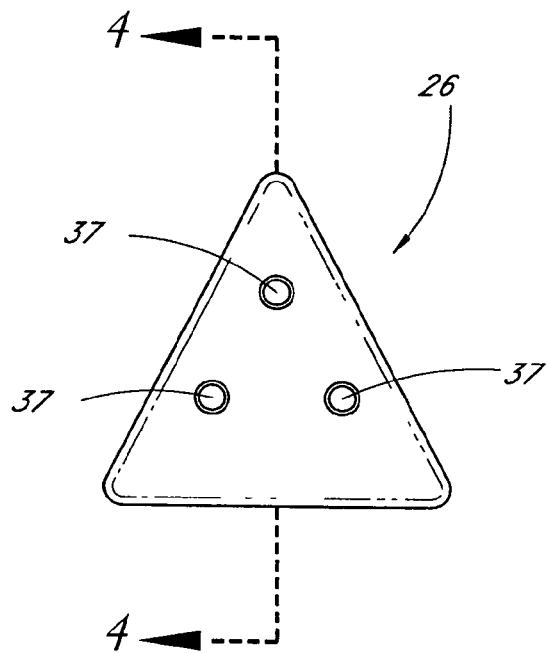
FIG. 3 is a front view of the locking plate of FIG. 1.
Figure 4:
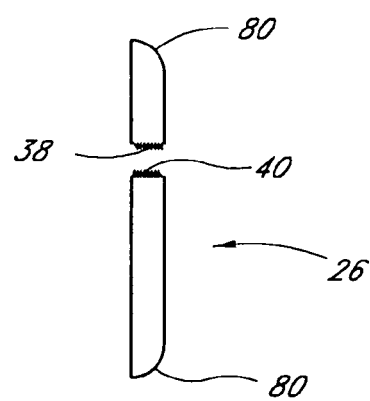
FIG. 4 is a cross-sectional view of the locking plate of FIG. 3 taken at line 4—4 of FIG. 3.

Referring to FIGS. 3 and 4, in the illustrated embodiment, the locking plate 26 comprises a plurality of openings 37, which form a tubular body or housing 38, for coaxial movement along the body 28. The housing 38 is provided with one or more surface structures 40 such as radially inwardly projecting teeth (e.g., threads) or flanges, for cooperating with complementary surface structures 42 on the body 28. The surface structures 40 and complementary surface structures 42 permit distal axial of the locking plate 26 with respect to the body 28, but resist proximal travel of the locking plate with respect to the body 28.

Figure 2A:
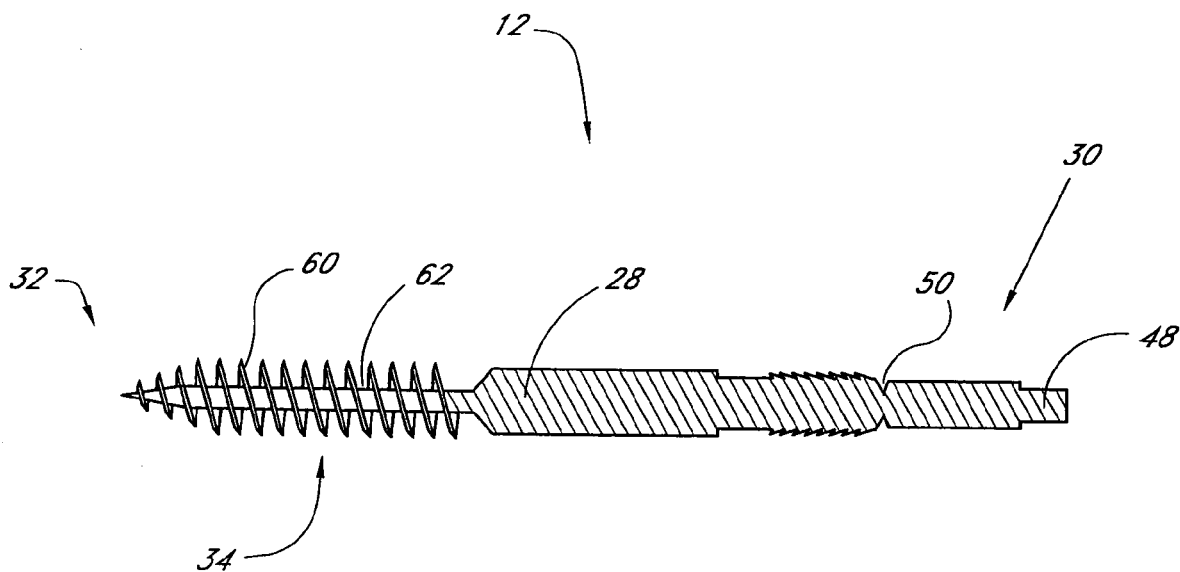
FIG. 2A is a side elevational cross section of a fixation pin similar to that of FIG. 1.
Figure 2B:
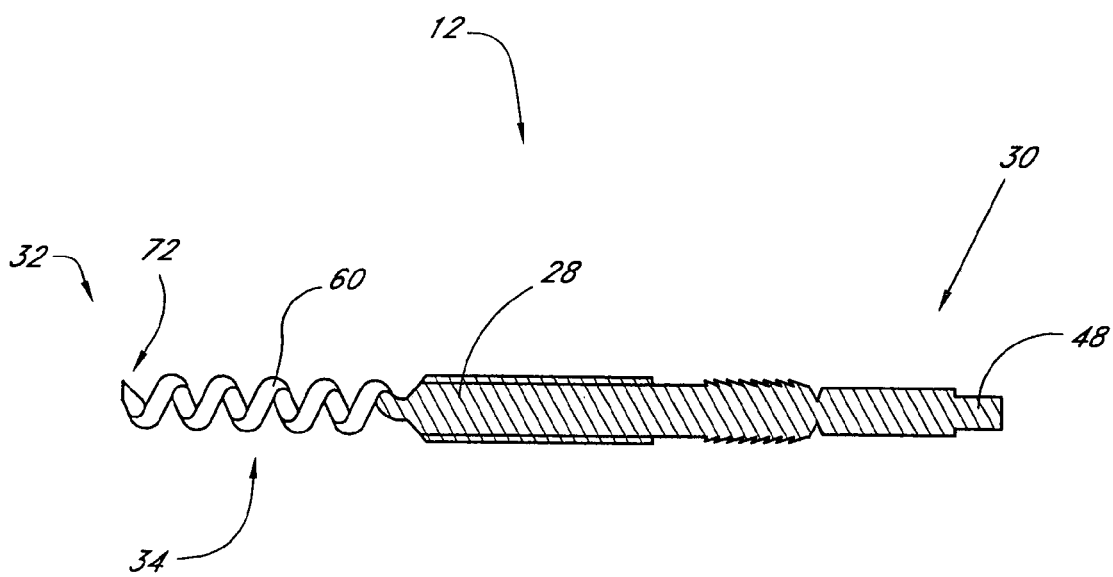
FIG. 2B is a side elevational cross section of a modified fixation pin similar to that of FIG. 2A.

As illustrated in FIG. 2A, retention structures 42 are spaced axially apart along the body 28, between a proximal limit 54 and a distal limit 56. The axial distance between proximal limit 54 and distal limit 56 is related to the desired axial working range of travel of the proximal anchor 36, and thus the range of functional sizes of the fixation device 12.

In one embodiment of the fixation device 12, the retention structure 42 comprise a plurality of threads, adapted to cooperate with the retention structures 40 on the locking plate 26, which may be a complementary plurality of threads. In this embodiment, the body 28 is distally advanced with respect to the locking plate 26 by rotation of the body 28 with respect to the locking plate 26. The body 28 may be advantageously removed from the locking plate 26 by reverse rotation, to permit removal of the body 28 from the patient. In this embodiment, the proximal end 30 of the body 28 is preferably provided with a rotational coupling 48 to permit a removal tool to rotate the body 28 with respect to the locking plate. Any of a variety of driving devices may be utilized, such as electric drills or hand tools which allow the clinician to manually rotate the cancellous bone anchor 34 into the head of the femur. Thus, the rotational coupling 48 may have any of a variety of cross sectional configurations, such as one or more flats or splines.

In one embodiment, the rotational coupling 48 comprises a proximal projection of the body 28 having a polygonal cross section, such as a hexagonal cross section. The rotational coupling 48 is illustrated as a male component, machined or milled or attached to the proximal end 30 of the body 28. However, the rotational coupling may also be in the form of a female element, such as a hexagonal or other noncircular cross sectioned lumen extending throughout a proximal portion or the entire length of the body 28. Although illustrated as solid throughout, the body 28 may be cannulated to accommodate installation over a placement wire as is understood in the art. The cross section of the central cannulation can be made non circular, e.g., hexagonal, to accommodate a corresponding male tool for installation or removal of the device regardless of the location of the proximal break point, as will be discussed.

In another embodiment, the body 28 is distally advanced with respect to the locking plate 26 without rotation of the body 28 with respect to the locking plate 26. In such an embodiment, any of a variety of complementary surface structures which permit one way ratchet like movement may be utilized, such as a plurality of annular rings or helical threads, ramped ratchet structures and the like for cooperating with an opposing ramped structure or pawl. Examples of such structures are described in U.S. patent application Ser. No. 09/990,587, filed Nov. 19, 2001, entitled "PROXIMAL ANCHORS FOR BONE FIXATION SYSTEM", which is hereby incorporated by reference herein. In some of these embodiments, an anti-rotation lock may be provided between the fixation device 12 and the locking plate 26, such as a spline or other interfit structure in the housing 38 to prevent relative rotation of the fixation device 12 following implantation.

In a modified embodiment, the surface structures 40 and complementary surface structures 42 may be toleranced to permit distal axial advancement onto the body 26 without rotation, but require rotation with respect to the locking plate 26 in order to remove the body 28.

Thus, the bone fixation system 11 can provide compression across a fracture throughout a range of motion following the placement of the distal anchor 34. The distal anchor 34 may be positioned within the cancellous and/or distal cortical bone, and the locking plate 26 may be distally advanced throughout a range to provide compression across the fracture without needing to relocate the distal anchor 34.

In many applications, the working range is at least about 10% of the overall length of the device, and may be as much as 20% or 30% or more of the overall device length. In the context of a femoral application, working ranges of up to about 10 mm may be provided, since estimates within that range can normally be readily accomplished within the clinical setting. In other applications, such as a metatarsal fracture, a working range in the area of from about 1 mm to about 2 mm may be all that is necessary. The embodiments disclosed herein can be scaled to have a greater or a lesser working range, as will be apparent to those of skill in the art in view of the disclosure herein.

With reference back to FIGS. 1, 2A, and 2B, the body 28 may be provided with at least one and preferably two or three or more break points 50 spaced axially apart along the proximal portion of the body 28. Break points 50 comprise a weakened transverse plane through the body 28, which facilitate severing of the proximal portion of the body 28 following proper tensioning of the locking plate. Break point 50 may be constructed in any of a variety of ways, such as by machining or milling an annular recess into the exterior wall of the body 28, or created one or more transverse perforations through the body 28 such as by mechanical, laser, or EDM drilling.

The body 28 may also be provided with at least one and preferably two or three or more graduation markings axially spaced along the proximal portion of the body 28. Such graduation markings can be used to indicate how far the body 28 has been inserted into the bone. Such graduation markings may include indicia indicating the distance (e.g., in millimeters or inches) from the proximal surface of the bone to the distal tip of the distal bone anchor 34.

The distal anchor 34 comprises a helical locking structure 60 for engaging cancellous and/or distal cortical bone. In the illustrated embodiment, the locking structure 60 comprises a flange that is be wrapped around a central core 62 or an axial lumen, as discussed below. The central core 62 or axial lumen defines a minor diameter of the helical locking structure 60. In a similar manner, the outer edge of the helical flange 60 defines a major diameter or outer boundary of the helical locking structure 60. The flange extends through at least one and generally from about two to about 50 or more full revolutions depending upon the axial length of the distal anchor and intended application. For most femoral neck fixation devices, the flange will generally complete from about 2 to about 20 revolutions. The helical flange 60 is preferably provided with a pitch and an axial spacing to optimize the retention force within cancellous bone, to optimize compression of the fracture.

The helical flange 60 of the embodiment illustrated in FIGS. 1 and 2A is shaped generally like a flat blade or radially extended screw thread. However, it should be appreciated that the helical flange 60 can have any of a variety of cross sectional shapes, such as rectangular, triangular or other as deemed desirable for a particular application through routine experimentation in view of the disclosure herein. The ratio of the major diameter to the minor diameter can be optimized with respect to the desired retention force within the cancellous bone and giving due consideration to the structural integrity and strength of the distal anchor 34. Another aspect of the distal anchor 34 that can be optimized is the shape of the major and minor diameters, which in the illustrated embodiment are generally cylindrical with a tapered distal end 32.

The distal end 32 and/or the outer edges of the helical flange 60 may be atraumatic (e.g., blunt or soft). This inhibits the tendency of the fixation device 12 to migrate anatomically proximally towards the hip joint bearing surface after implantation (i.e., femoral head cut-out). Distal migration is also inhibited by the dimensions and presence of the proximal anchor 36, which has a larger footprint than conventional screws.

Referring to FIG. 2B, a variation of the distal anchor 34 is illustrated. The distal anchor 34 comprises an elongated helical locking structure 60 that is spirally wrapped about an axial lumen through at least one and preferably from about two to about 20 or more full revolutions. The axial lumen defines a minor diameter that is generally cylindrical. As with the previous embodiment, the elongated body 60 is provided with a pitch and an axial spacing to optimize the retention force within cancellous bone, which optimizes compression of the fracture. The tip 72 of the elongated body 60 may be pointed. Although not illustrated, this variation is particularly suited for a canulated fixation device 12. That is, a design wherein a central lumen extends through the body 28 and the distal anchor 34.

Additional configurations of the distal anchor are described in co-pending U.S. patent application Ser. No. 10/012,687, filed Nov. 13, 2001, entitled "DISTAL BONE ANCHORS FOR BONE FIXATION WITH SECONDARY COMPRESSION", which is hereby incorporated by reference herein.

With reference to FIGS. 3 and 4, the illustrated embodiment of the locking plate 26 includes the three openings 37. More specifically, in the illustrated embodiment, each opening 37 is positioned generally at the apex of a generally equilateral triangle, which has a lower base positioned along a generally horizontal axis. However, it should be appreciated that, in other embodiments, the locking plate 26 can include as few as one or two openings. In other embodiments, the three openings 37 can be arranged into other triangular shapes (e.g., a right or isosceles triangle) with various orientations. In still other embodiments, the locking plate 26 can include more than three openings (e.g., 4, 5 or 6) and which may be in the form in any of a number of various shapes (e.g., squares, rectangles, crosses, etc.) or combinations of shapes.

In the illustrated embodiment, the locking plate 26 has a generally triangular shape so as to provide a generally uniform border around the openings 37 while generally minimizing the size of the locking plate. However, it should be appreciated that the locking plate can be formed into a variety of other shapes. The locking plate preferably has beveled edges 80 as best seen in FIG. 4. The border will generally have a width of at least about 4 mm and often within the range of from about 4 mm to about 20 mm or more greater. In a modified embodiment, the locking plate can be curved to match the curved shape of the femur and further optimize the footprint or contact surface area between the locking plate and the femur.

In the embodiment illustrated in FIG. 1, the bone contacting surface 84 of the locking plate 26 resides in or approximately on a plane which is inclined with respect to the longitudinal axis of the bodies 28. Any of a variety of angular relationships between the bone contacting surface 84 of the locking plate 26 and the longitudinal axis of the body 28 and the housing 38 may be utilized, depending upon the anticipated entrance angle of the body 28 and associated entrance point surface of the femur 10. In general, the longitudinal axis extending through the head 14 and neck 16 of the human femur is inclined at an angle of approximately 126° from the longitudinal axis of the long body 17 of the femur 10. Angles between the longitudinal axis of body 28 and tissue contacting surface 84 within the range of from about 90° to about 140° will generally be utilized, often within the range of from about 100° to about 120°, for fixed angle fixation devices. A perpendicular locking plate 26 (i.e., 90°) is illustrated in FIGS. 3 and 4.

The clinician can be provided an array of locking plates 26 of varying angular relationships between the bone contacting surface 84 and the longitudinal axis of the body 28 and housing 38 (e.g., 90°, 100°, 110°, 120°, and 130°). A single body 28 can be associated with the array such as in a single sterile package. The clinician upon identifying the entrance angle of the body 28 and the associated entrance point surface orientation of the femur 10 can choose the locking plate 26 from the array with the best fit angular relationship, for use with the body 28.

In the illustrated embodiments, the locking late 26 is arranged such that the angular relationship between the bone contacting 84 surface and the longitudinal axis of the housing 38 of two or more of the bodies 28 are parallel to each other. However, in a modified embodiment, two or more the angular relationships between bodies 28 may deviate from parallel. For example, in one embodiment, the locking plate is configured such that longitudinal axis of two or more housings 38 are not parallel to each other and are within a range of approximately 0 to 60 degrees with respect to each other.

Figure 5:
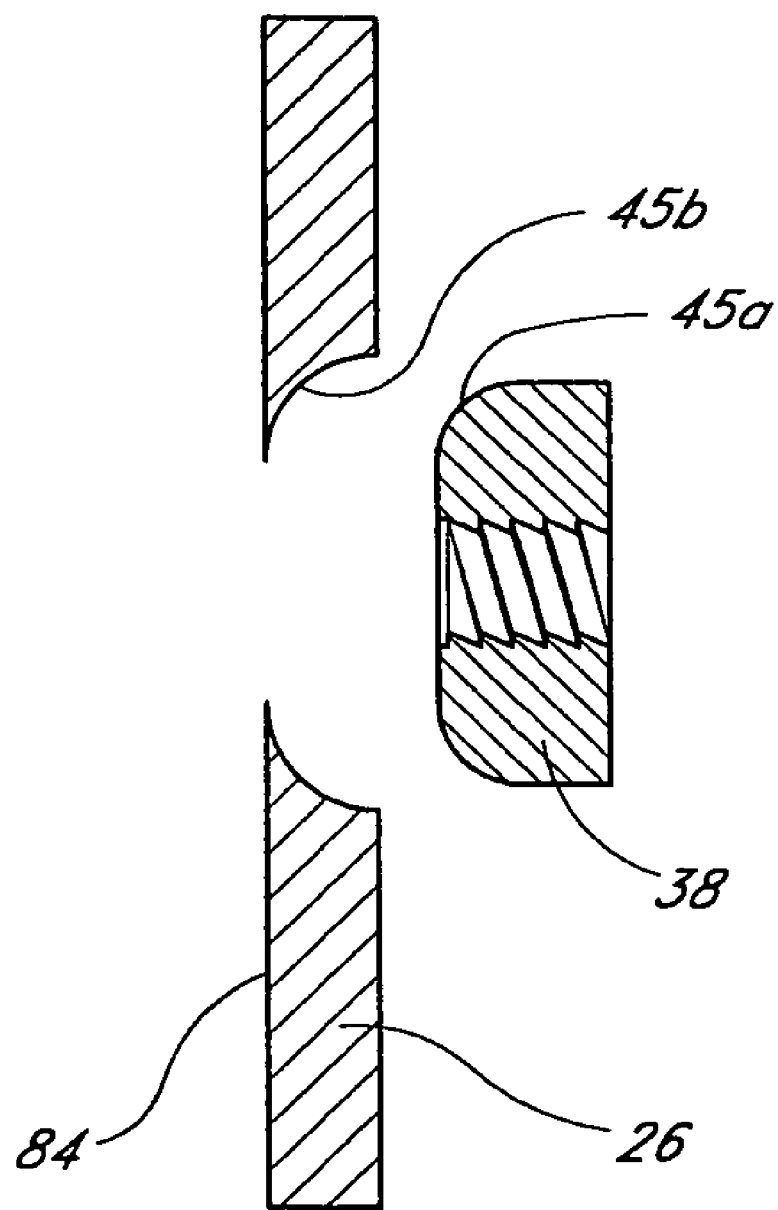
FIG. 5 is a cross sectional view through a modified locking plate with an angularly adjustable housing.

In accordance with an optional feature, illustrated in FIG. 5, the locking plate 26 can be configured such that the body 28 can be angularly adjustable with respect to the bone contacting surface 84. More specifically, in this embodiment, the housing 38 is a separate component from the locking plate 26. The housing 38 and the locking plate 26 preferably include corresponding semi-spherical or radiused surfaces 45a, and 45b. The surface 45b surrounds an aperture 49 in the locking plate 26. This arrangement allows the housing 38 to extend through and pivot with respect to the locking plate 26. As such, the angular relationship between the bone contacting surface 84 of the locking plate 26 and the longitudinal axis of the body 28 can vary in response to the entrance angle.

In use, the clinician first identifies a patient having a fracture to be treated, such as a femoral neck fracture, which is fixable by an internal fixation system. The clinician accesses the proximal femur, reduces the fracture if necessary and selects a bone drill and drills a plurality of holes 90 in accordance with conventional techniques. In the example of a femoral neck fracture, three holes and fixation devices will often be used as has been discussed. Preferably, the hole 90 has a diameter within the range from about 3 mm to about 8 mm. This diameter may be slightly larger than the diameter of the distal anchor 34. The hole 90 preferably extends up to or slightly beyond the fracture 24.

A fixation pin 12 having an axial length and outside diameter suitable for the hole 90 is selected. The distal end 32 of the fixation pin 12 is advanced distally into the hole 90 until the distal anchor 34 reaches the distal end of the hole 90. The locking plate 26 may be carried by the fixation pin 12 prior to advancing the body 28 into the hole 90, or may be attached following placement of one or more of the bodies 28 within the holes 90. Once the body 28 is in place, the clinician may use any of a variety of driving devices, such as electric drills or hand tools to rotate the cancellous bone anchor 34 into the head of the femur. In one embodiment, the elongated bodies are rotated sequentially or simultaneously into position across the fracture 24 or separation between adjacent bones and into the adjacent bone or bone fragment. The locking plate 26 is then distally advanced by applying proximal traction to the proximal end 20 of the body 28 to apply secondary compression and lock the system 11 into place.

While proximal traction is applied to the proximal end 30 of body 28, such as by conventional hemostats, pliers or a calibrated loading device, the locking plate 26 is advanced distally until the locking plate 26 fits snugly against the outer surface of the femur or tissue adjacent the femur. Appropriate compression of the fixation system 11 across the fracture is accomplished by tactile feedback or through the use of a calibration device for applying a predetermined load on the implantation device. One advantage of the structure of the present invention is the ability to adjust compression independently of the setting of the distal anchor 34.

Following appropriate tensioning of the locking plate 26, the proximal extension 30 of the body 28 is preferably cut off, snapped off, unscrewed or otherwise removed. Body 28 may be cut using conventional saws, cutters or bone forceps which are routinely available in the clinical setting. Alternatively, the fixation device can be selected such that it is sized to length upon tensioning, so that no proximal projection remains.

Following removal of the proximal end 30 of body 28, the access site may be closed and dressed in accordance with conventional wound closure techniques.

Preferably, the clinician will have access to an array of fixation systems 11, having, for example, different diameters, axial lengths, angular and spatial relationships. These may be packaged one per package in sterile envelopes or peelable pouches, or in dispensing cartridges which may each hold a plurality of systems 11. Upon encountering a fracture for which the use of a fixation device is deemed appropriate, the clinician will assess the dimensions and load requirements, and select a fixation system from the array which meets the desired specifications.

Figure 6:
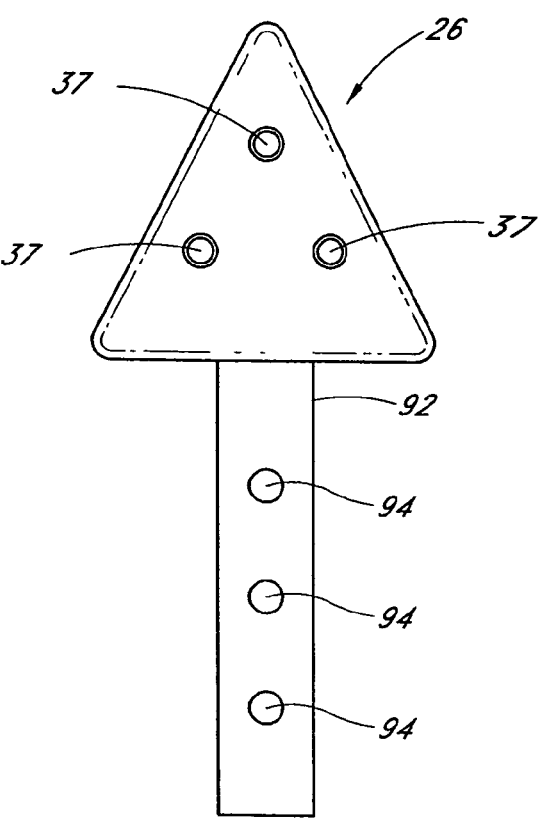
FIG. 6 is a front view of a locking plate as in FIG. 3 in combination with a side plate.
Figure 7:
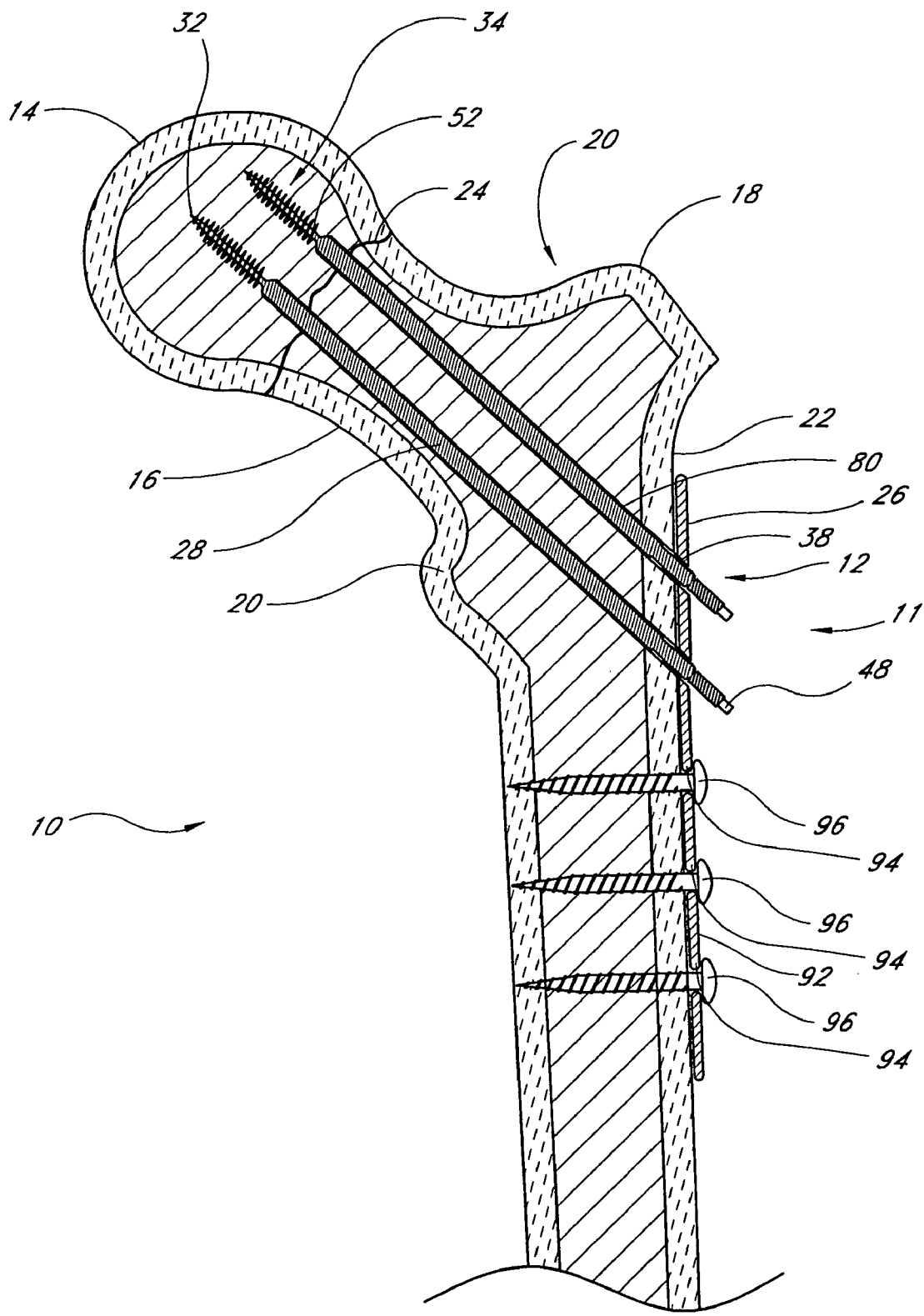
FIG. 7 is a cross section through a proximal portion of the femur, illustrating the use of fixation pins in combination with the locking plate and side plate of FIG. 6.

With reference now to FIG. 6, the locking plate 26 can be used with an elongated side support or plate 92, which, in the illustrated arrangement, extends longitudinally below the openings 37 of the locking plate 26. The elongated side plate 92 preferably includes one or more openings 94 for receiving one or more femoral shaft screws 96 as shown in FIG. 7. Advantageously, the elongated side plate 92 spreads the forces across a larger area of the femur 17, which affects the distribution of load and increases the overall stability of the locking plate 26 and the fixation system 11. In a modified embodiment, the elongated side plate can 92 can in addition or in the alternative extend above the locking plate 96 and include one or more openings above the locking plate 26 for receiving trochanteric anchor screws (not shown).

The side plate 92 may also inhibit proximal movement of the locking plate 26 with respect to the bone. This allows the bone fixation system 11 to capture "secondary compression" of the fracture. That is, the bone fixation system 11 can be used to provide an initial compression across the fracture when the locking plate 26 is appropriately tensioned. However, as the patient applies weight or stress to the bone post procedure, the fracture typically undergoes secondary compression, which further compresses the fracture. During such secondary compression, the side plate 92 prevents proximal movement of the locking plate 26 with respect to the bone. The ratchet-type structures 40, 42 of the locking plate 26 and the body 28 allow the locking plate 26 to move distally along the body 28. Thus, any slack caused by the secondary compression is taken up by the locking plate as the retention structures 40, 42 prevent proximal movement of the locking plate 26 with respect to the body 28. This system 11 is therefore self tightening after it has been implanted in the patient.

Figure 8:
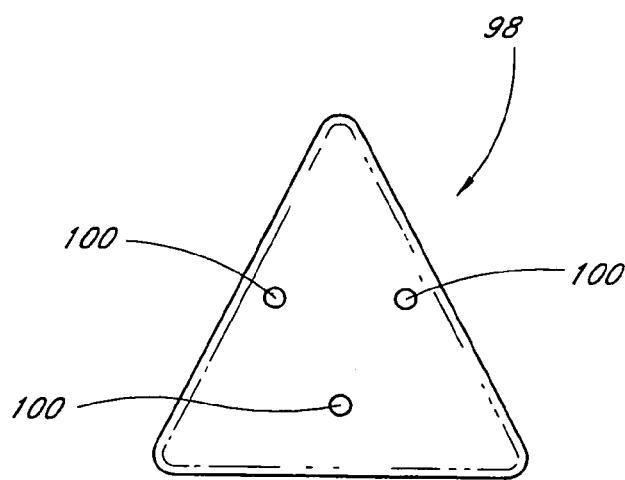
FIG. 8 is a front view of a locking plate cap.
Figure 9:
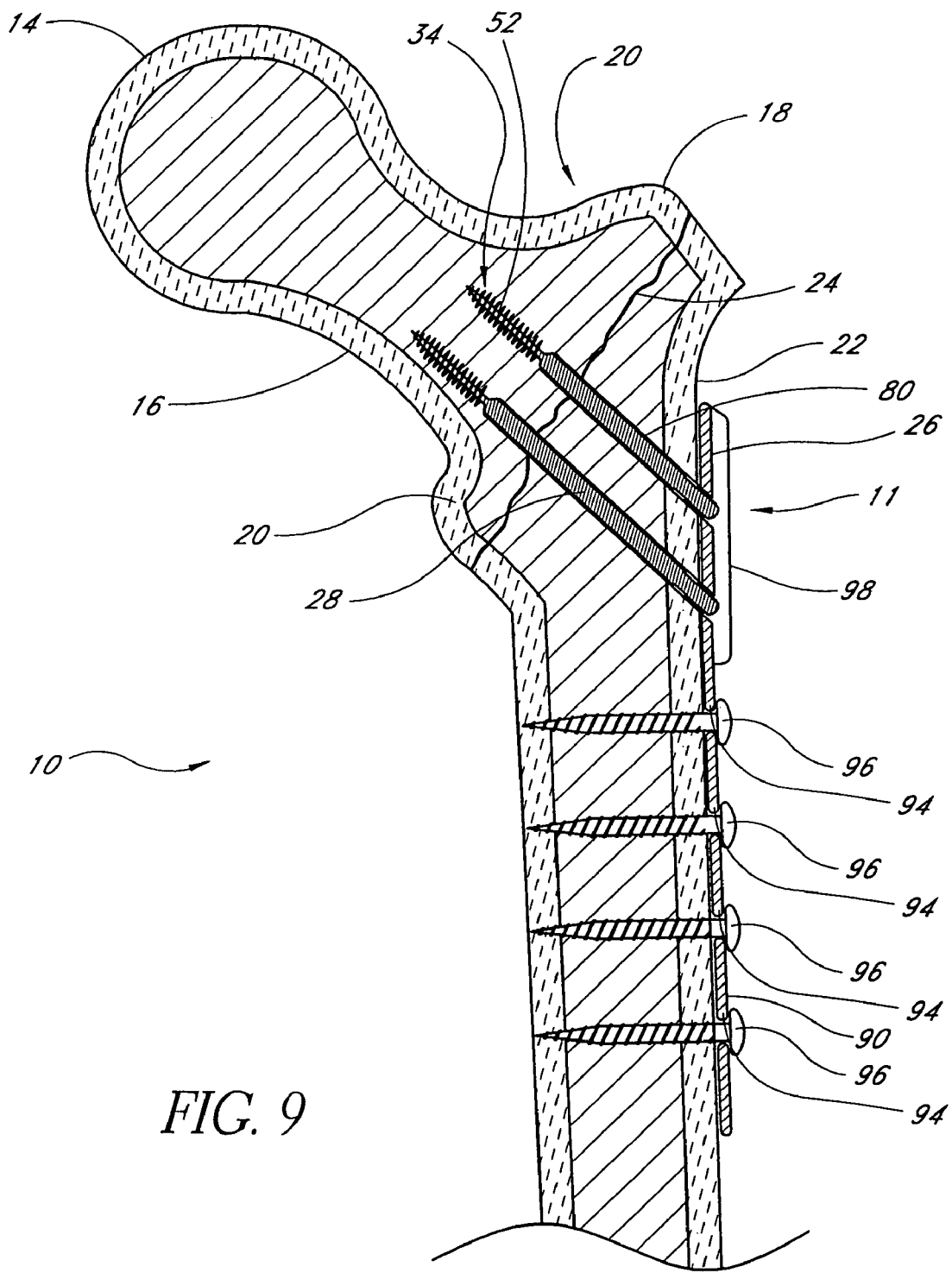
FIG. 9 is a cross section through a proximal portion of the femur, illustrating the use of fixation pins in combination with a locking plate and side plate as in FIG. 6 and a locking plate cap as in FIG. 8.

FIG. 8 illustrates a locking cover cap 98 that may be used with the locking plates 26 described above. The locking cover cap 96 is preferably configured to cover the locking plate 26 and, therefore, has a shape that closely approximates the shape of the locking 26. The locking cover cap 98 includes one or more openings 100 for receiving one or more locking set screws (not shown). The locking plate 98 preferably also includes one or more openings for receiving the set screws. After proper tensioning of the fixation pins 12 and severing of the proximal portion of the body 28, the locking set screws may be used to secure the locking cover cap 98 to the locking plate 26 as shown in FIG. 9. Advantageously, the locking cover cap 98 prevents the body 28 from backing out of the locking plate 96.

Figure 10:
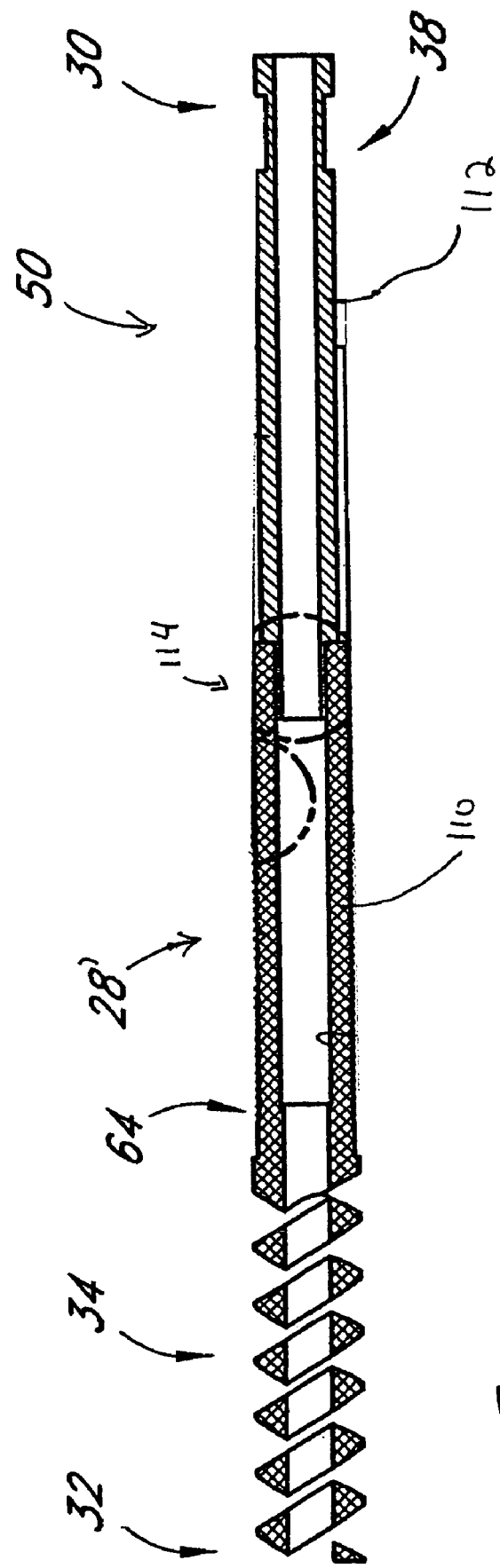
FIG. 10 is a cross-sectional side view of another embodiment of a fixation pin.

FIG. 10 illustrates a modified embodiment of the body 28', which can be used with the locking plates described above. In the illustrated embodiment, the body 28' comprises a first portion 110 and a second portion 112 that are coupled together at a junction 114. In the illustrated embodiment, the first portion 110 carries the distal anchor 34 while the second portion 112 forms the proximal end 30 of the body 28'. The first and second portions 110,112 are preferably detachably coupled to each other at the junction 114. In the illustrated embodiment, the first and second portions 110, 112 are detachably coupled to each other via interlocking threads.

In a modified arrangement, the second portion 112 can comprise any of a variety of tensioning elements for permitting proximal tension to be placed on the distal anchor 34 while the proximal anchor is advanced distally to compress the fracture. For example, any of a variety of tubes or wires can be removably attached to the first portion 110 and extend proximally to a proximal handpiece. In one such arrangement, the first portion 110 can include a releasable connector in the form of a latching element, such as an eye or hook. The second portion 110 can include a complementary releasable connector (e.g., a complementary hook) for engaging the first portion 100. In this manner, the second portion 112 can be detachably coupled to the first portion 10 such proximal traction can be applied to the first portion 110 through the second portion. Alternatively, the second portion 112 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein. Additional configurations of the body 28' can be found in U.S. patent application Ser. No. 09/991,367, filed on Nov. 13, 2001, entitled "METHOD AND APPARATUS FOR BONE FIXATION WITH SECONDARY COMPRESSION", which is hereby incorporated in its entirety by reference herein.

Following appropriate tensioning of the fixation device 12, the second portion 112 of the body 28' is preferably detached from the first portion 112 and removed. In the illustrated embodiment, this involves rotating the second portion 112 with respect to the first portion 110.

Figure 11:
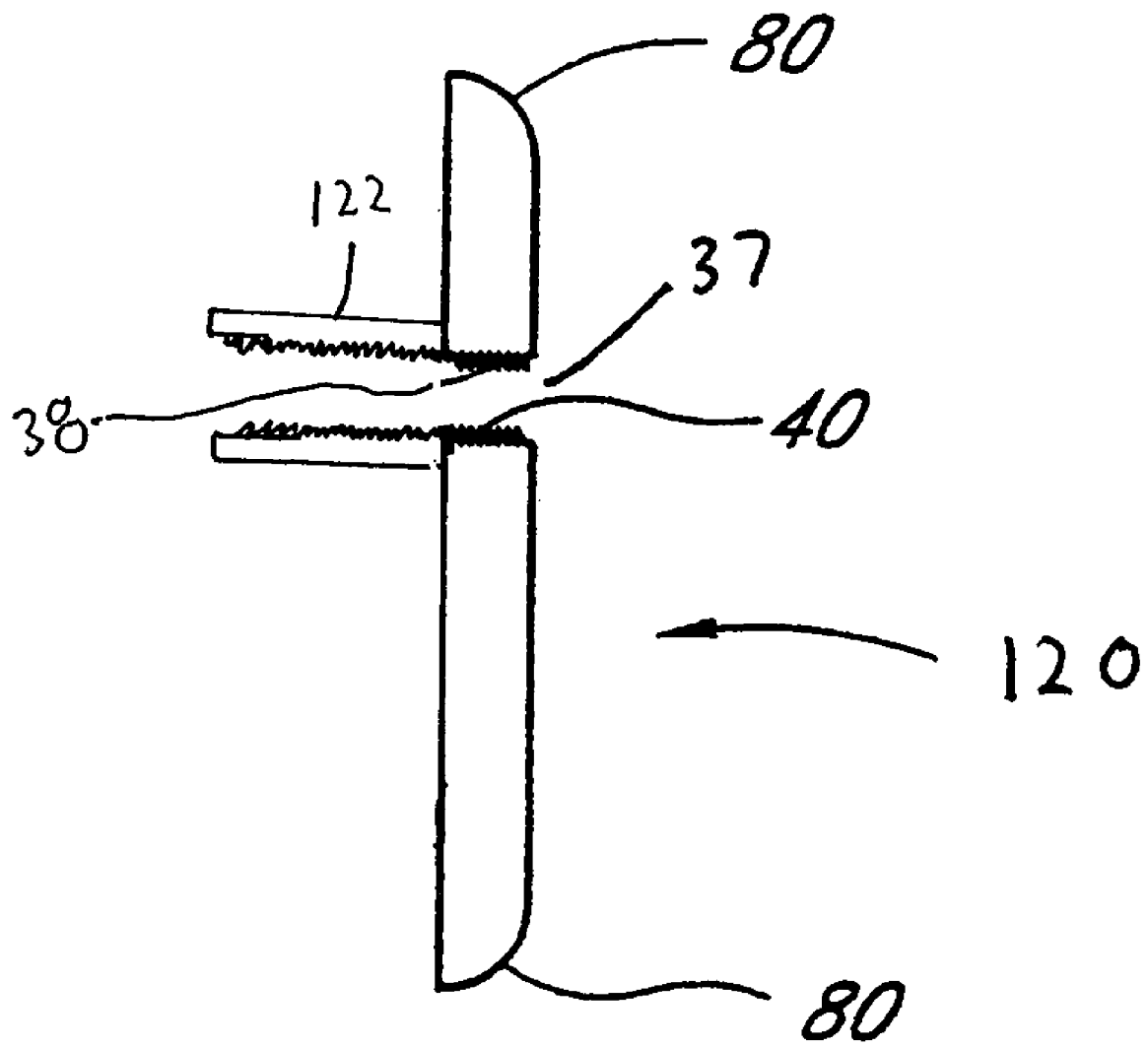
FIG. 11 is a cross-sectional view of another embodiment of a locking plate.
Figure 12:
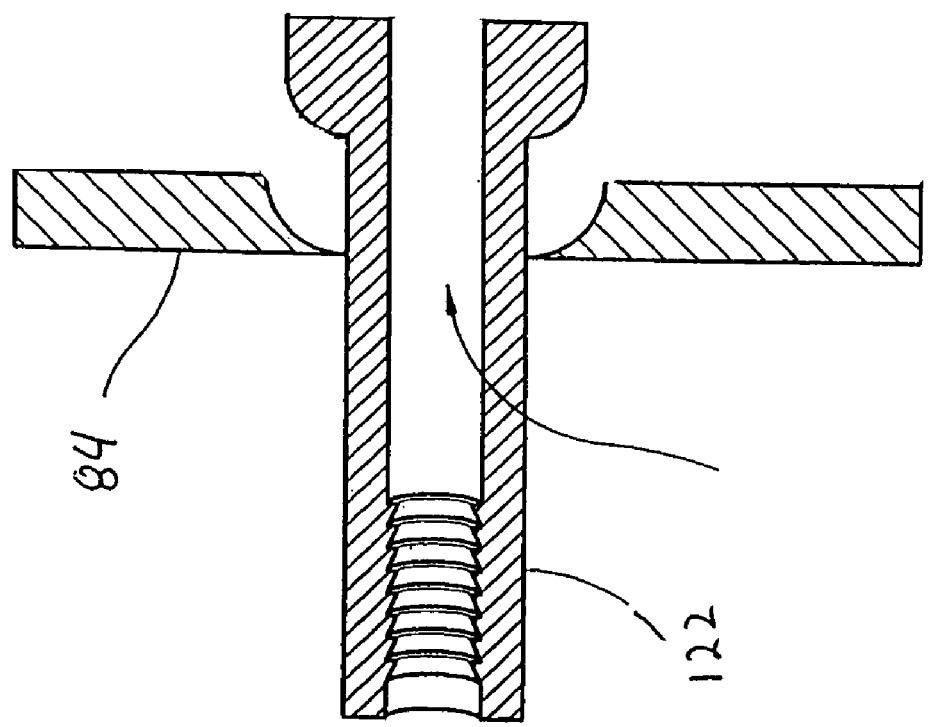
FIG. 12 is cross-sectional view another embodiment of a locking plate

The two-piece body 28' described above may be used with a modified locking plate 120, which is illustrated in FIG. 11. The modified locking plate 120 includes a plurality of openings 37 as described above. In addition, each opening is preferably defined, in part, by a tubular extension 122, which extends from the bone contacting surface 84 of the locking plate 120. Preferably, the surface structures 40 extend into the tubular extension 122 so as to provide the fixation plate 12 with an increased working range. It should be appreciated that the embodiments described above with respect to FIGS. 10 and 11 may be combined with many of the features of the embodiments described above with respect to FIGS. 1–9. For example, the tubular extensions 122 may not be parallel to each other and may be within the range of 0 to 60 degrees. In another embodiment illustrated in FIG. 12, the tubular extension 122 can be angularly adjustable with respect to the bone contacting surface 84. More specifically, in this embodiment, the housing 38 is a separate component from the locking plate 26.

The fixation systems of the present invention and their various components (e.g., fixation pins, 12, locking plates 26 and locking cover caps 98) may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful:

(1) the blend of poly(p-dioxanone) and a lactide/glycolide copolymer, as disclosed in U.S. Pat. No. 4,646,741 which is incorporated by reference.

(2) the glycolide-rich blend of two or more polymers, one polymer being a high lactide content polymer, and the other being a high glycolide content disclosed in U.S. Pat. No. 4,889,119 which is incorporated by reference.

Additional bioabsorbable materials are disclosed in copending application Ser. No. 09/558,057 filed Apr. 26, 2000, the disclosure of which is incorporated in its entirety herein by reference.

The fixation devices and plates may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate in a bioabsorbable construction. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A femoral neck fracture fixation system, comprising:
 a plurality of elongated bodies, each having a proximal end and a distal end;

a distal anchor on the distal end of each of the elongated bodies;

a first retention structure on the elongated bodies, proximal to the distal anchor; and a plate with a plurality of openings, the plate being moveably carried by the plurality elongated bodies, and wherein the plate is movable in the distal direction with respect to the elongated bodies and the first retention structure resists proximal movement of the plate with respect to the elongated bodies and wherein each elongated body comprises first portion and a second portion that are detachably coupled to each other at a junction.

2. A femoral neck fracture fixation device as in claim 1, wherein the distal anchor comprises a helical flange.

3. A femoral neck fracture fixation device as in claim 1, wherein the first retention structure comprises an annular structure.

4. A femoral neck fracture fixation device as in claim 1, wherein the plate includes at least three openings arranged in a triangular pattern.

5. A femoral neck fracture fixation device as in claim 1, further comprising a side plate that extends from the plate.

6. A femoral neck fracture fixation device as in claim 5, wherein the side plate includes a plurality of openings for receiving femoral shaft screws.

7. A femoral neck fracture fixation device as in claim 6, wherein the plurality of openings are located approximately 8 to 18 millimeters apart from each other.

8. A femoral neck fracture fixation device as in claim 6, wherein the plurality of openings are located at least 2 to 5 millimeters from an outer edge of the plate.

9. A bone fracture fixation device, comprising:
at least two of elongated bodies, each having a proximal end and a distal end;
a cancellous bone anchor on the distal end of each of the two the elongated bodies;
a plate having at least two openings and being axially movably mountable on the elongated bodies; and
complimentary surface structures in between the elongated bodies and the plate that permit advancing the plate in the distal direction to apply compression across a fracture but that resist axial proximal movement of the plate with respect to the elongated bodies.

10. A bone fracture fixation device as in claim 9, wherien each elongated body comprises first portion and a second portion that are detachably coupled to each other at a junction.

11. A bone fracture fixation device as in claim 10, wherein each of the openings is associated with a tubular sleeve that in a first position extends distally past the junction between the first portion and the second portion.

12. A bone fracture fixation device as in claim 10, wherein the cancellous bone anchor comprises a helical flange.

13. A bone fracture fixation device as in claim 9, wherein the complimentary surface structures comprise an annular structure.

14. A bone fracture fixation device as in claim 9, wherein the complimentary surface structures comprise a flange.

15. A bone fracture fixation device as in claim 9, wherein the complimentary surface structures comprise a thread.

16. A bone fracture fixation device as in claim 9, wherein the plate includes at least three openings arranged in a triangular pattern.

17. A bone fracture fixation device as in claim 9, further comprising a cap configured to cover the ate least two openings in the plate.

18. A bone fracture fixation device as in claim 17, further comprising at least one set screw for coupling the cap to the plate.

19. A bone fracture fixation device as in claim 9, further comprising a side plate that extends from the plate.

20. A bone fracture fixation device as in claim 19, wherein the side plate includes a plurality of openings for receiving femoral shaft screws.

21. A bone fracture fixation device as in claim 9, wherein the at least two openings are located approximately 8 to 18 millimeters apart from each other.

22. A bone fracture fixation device as in claim 9, wherein the at least two openings are located at least 2 to 4 millimeters from an outer edge of the plate.

23. A bone fracture fixation device as in claim 9, wherein each of the at least two openings define a tubular portion.

24. A bone fracture fixation device as in claim 23, wherein each of tubular portions define a longitudinal axis and at least two of the longitudinal axes are parallel to each other.

25. A bone fracture fixation device as in claim 23, wherein each of tubular portions define a longitudinal axis and at least two of the longitudinal axes are not parallel to each other.

26. A bone fracture fixation device as in claim 23, wherein each of tubular portions define a longitudinal axis which forms an angle with a bone contacting face of the plate, the angle being in the range of about 90 degrees to 150 degrees.

27. A bone fracture fixation device as in claim 9, wherein each of the at least two openings is formed within a housing that is angularly adjustable with respect to the plate.

28. A femoral neck fracture fixation system, comprising:
a plurality of elongated bodies, each having a proximal end and a distal end;
a distal anchor on the distal end of each of the elongated bodies;
a first retention structure on the elongated bodies, proximal to the distal anchor; and
a plate with a plurality of openings, the plate being moveably carried by the plurality elongated bodies, and
wherein the plate is movable in the distal direction with respect to the elongated bodies and the first retention structure resists proximal movement of the plate with respect to the elongated bodies and wherein the plate includes at least three openings arranged in a triangular pattern.

29. A femoral neck fracture fixation device as in claim 28, wherein the distal anchor comprises a helical flange.

30. A femoral neck fracture fixation device as in claim 28, wherein the first retention structure comprises an annular structure.

31. A femoral neck fracture fixation device as in claim 28, further comprising a side plate that extends from the plate.

32. A femoral neck fracture fixation device as in claim 31, wherein the side plate includes a plurality of openings for receiving femoral shaft screws.

33. A femoral neck fracture fixation device as in claim 32, wherein the plurality of openings are located approximately 8 to 18 millimeters apart from each other.

34. A femoral neck fracture fixation device as in claim 32, wherein the plurality of openings are located at least 2 to 5 millimeters from an outer edge of the plate.

* * * * *

UNITED STATES PATENT AND TRADEMARK OFFICE
CERTIFICATE OF CORRECTION

| | | |
|---|---|---|
| PATENT NO. | : 7,070,601 B2 | Page 1 of 1 |
| APPLICATION NO. | : 10/756892 | |
| DATED | : July 4, 2006 | |
| INVENTOR(S) | : Bruce E. Stevens | |

It is certified that error appears in the above-identified patent and that said Letters Patent is hereby corrected as shown below:

Column 3, Line 13 after "end" insert --of--.

Column 4, Line 9 after "view" insert --of--.

Column 4, Line 10 after "plate" insert --.--.

Column 11, Line 61 after "plate" delete "can".

Column 15, Line 37 in Claim 9, after "two" insert --of--.

Column 15, Line 45 in Claim 10, delete "wherien" and insert --wherein--, therefor.

Column 15, Line 66 in Claim 17, before "least" delete "ate" and insert --at--, therefor.

Signed and Sealed this

Third Day of April, 2007

JON W. DUDAS
*Director of the United States Patent and Trademark Office*